United States Patent
Seal et al.

(10) Patent No.: US 12,422,294 B2
(45) Date of Patent: ***Sep. 23, 2025

(54) BIOCONTAINER ASSEMBLY FOR BIOPROCESSING SYSTEM

(71) Applicant: CYTIVA US LLC, Marlborough, MA (US)

(72) Inventors: Michael B. Seal, Hampshire (GB); Matthew J. Loveless, Hampshire (GB)

(73) Assignee: Cytiva US LLC, Marlborough, MA (US)

( * ) Notice: Subject to any disclaimer, the term of this patent is extended or adjusted under 35 U.S.C. 154(b) by 928 days.

This patent is subject to a terminal disclaimer.

(21) Appl. No.: 17/127,042

(22) Filed: Dec. 18, 2020

(65) Prior Publication Data

US 2021/0199484 A1 Jul. 1, 2021

Related U.S. Application Data

(60) Provisional application No. 62/955,827, filed on Dec. 31, 2019.

(51) Int. Cl.
| | |
|---|---|
| *G01F 22/00* | (2006.01) |
| *A61J 1/10* | (2006.01) |
| *C12M 1/00* | (2006.01) |
| *G01F 23/263* | (2022.01) |

(52) U.S. Cl.
CPC ............... *G01F 22/00* (2013.01); *A61J 1/10* (2013.01); *C12M 23/14* (2013.01); *G01F 23/265* (2013.01); *G01F 23/266* (2013.01)

(58) Field of Classification Search
CPC ...... G01F 22/00; G01F 23/265; G01F 23/266; C12M 23/14
See application file for complete search history.

(56) References Cited

U.S. PATENT DOCUMENTS

| | | |
|---|---|---|
| 5,135,485 A | 8/1992 | Cohen et al. |
| 7,320,416 B2 | 1/2008 | Miller et al. |
| 7,509,856 B1 | 3/2009 | Winkens et al. |
| 9,658,095 B2 | 5/2017 | Winkens et al. |
| 10,233,417 B2 | 3/2019 | Keitel et al. |

(Continued)

FOREIGN PATENT DOCUMENTS

| | | |
|---|---|---|
| CA | 2 836 218 A1 | 6/2015 |
| CN | 1860217 A | 11/2006 |

(Continued)

OTHER PUBLICATIONS

David Wang, TI Designs: Capacitive-Based Liquid Level Sensing Sensor Reference Design, Mar. 2015, (Year: 2015).*

(Continued)

*Primary Examiner* — Neil N Turk
(74) *Attorney, Agent, or Firm* — Leydig, Voit & Mayer, Ltd.

(57) ABSTRACT

A biocontainer assembly includes a biocontainer bag, a support frame, and a capacitive fill level sensor. The biocontainer bag defines a storage volume. The support frame includes a shelf having a support surface disposed at an oblique angle with respect to a horizontal axis. The capacitive fill level sensor is mounted to the support surface and is configured to generate a fill level signal indicative of the amount of material within the storage volume of the biocontainer bag.

18 Claims, 8 Drawing Sheets

(56) References Cited

U.S. PATENT DOCUMENTS

| | | |
|---|---|---|
| 11,142,742 B2 | 10/2021 | Kawasaki et al. |
| 2004/0259239 A1 | 12/2004 | Branson et al. |
| 2007/0113474 A1* | 5/2007 | Everett .................. C12M 21/02 47/65.8 |
| 2008/0299013 A1* | 12/2008 | Trieu ..................... B01L 9/527 422/400 |
| 2009/0212178 A1* | 8/2009 | Westberg .............. A61M 1/167 248/176.1 |
| 2010/0005903 A1 | 1/2010 | Beavis |
| 2010/0209966 A1 | 8/2010 | Everett et al. |
| 2013/0157355 A1 | 6/2013 | Barrett et al. |
| 2015/0151261 A1 | 6/2015 | Isailovic |
| 2015/0165399 A1 | 6/2015 | Rawlings |
| 2015/0322399 A1 | 11/2015 | Purushothaman et al. |
| 2016/0047683 A1 | 2/2016 | Winkens et al. |
| 2016/0296897 A1 | 10/2016 | Marshall |
| 2016/0303567 A1 | 10/2016 | Seal et al. |
| 2016/0304822 A1 | 10/2016 | Seal et al. |
| 2017/0191861 A1 | 7/2017 | Rondano et al. |
| 2017/0284584 A1 | 10/2017 | Kesselaar et al. |
| 2018/0078911 A1 | 3/2018 | Marshall |
| 2018/0347709 A1 | 12/2018 | Bowdery |
| 2019/0017011 A1 | 1/2019 | Patil et al. |
| 2021/0197142 A1 | 7/2021 | Seal et al. |
| 2021/0197189 A1 | 7/2021 | Isailovic et al. |
| 2021/0199679 A1 | 7/2021 | Seal et al. |

FOREIGN PATENT DOCUMENTS

| | | | |
|---|---|---|---|
| CN | 102604825 A | 7/2012 | |
| CN | 105164505 A | 12/2015 | |
| DE | 102013005963 A1 | 10/2014 | |
| DE | 102013109820 A1 | 3/2015 | |
| EP | 1 739 165 A1 | 6/2005 | |
| EP | 2 607 474 B1 | 12/2012 | |
| GB | 2323671 A * | 9/1998 | .......... G01F 23/266 |
| JP | 2001-333922 A2 | 12/2001 | |
| JP | 2012-517829 T | 8/2012 | |
| JP | 2016-059319 A2 | 9/2014 | |
| JP | 2017-079633 A2 | 10/2015 | |
| JP | 2019-505214 A | 2/2019 | |
| WO | WO-2015200269 A1 * | 12/2015 | ............. B01D 61/20 |
| WO | 2018/212029 A1 | 11/2018 | |

OTHER PUBLICATIONS

English language translation of Office Action issued in Chinese counterpart application No. 202011614630.X; 6 pages; Apr. 19, 2022.

Singapore Patent Office, Search Report in Singapore counterpart application No. 10202013221V; 3 pages; Jan. 25, 2022.

European Patent Office, Search Report in European Patent Application No. 20 21 6876, 11 pages, May 12, 2021.

English-language translation of Nov. 24, 2021 Office Action issued in Japanese counterpart patent application No. P2020-215380.

Pall Life Sciences, "Allegro™ Bioprocessing Workstations" Document No. USD2793b (2015).

* cited by examiner

BIOCONTAINER ASSEMBLY FOR BIOPROCESSING SYSTEM

CROSS-REFERENCE TO RELATED APPLICATIONS

This patent application claims the benefit of priority to U.S. Provisional Patent Application No. 62/955,827, filed Dec. 31, 2019, and entitled, "Biocontainer Assembly for Bioprocessing System," which is incorporated in its entirety herein by this reference.

BACKGROUND OF THE INVENTION

A buffer management system typically includes a number of biocontainer bags that contain buffer solution for use in a bioprocessing application. Conventional buffer management systems use weigh scales, typically load cells, to determine weights of liquids within the biocontainer bags for liquid level detection, which is transmitted to an automation system. The weight detected by the weigh scale is converted into a calculated volume value using a conversion factor. This technique, however, may not provide precise liquid volume detection capabilities as the actual volume of the liquid of a given weight can vary with the specific gravity of the liquid within the biocontainer bag. The load cells can also present a significant cost, particularly when the system includes multiple volume measurement requirements.

There is a continued need in the art to provide additional solutions to enhance the management of buffer solutions used in various bioprocessing applications.

It will be appreciated that this background description has been created by the inventors to aid the reader, and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims, and not by the ability of any disclosed feature to solve any specific problem noted herein.

BRIEF SUMMARY OF THE INVENTION

The present disclosure, in one aspect, is directed to embodiments of a biocontainer assembly used in a buffer management system for a bioprocessing system. In embodiments, the biocontainer assembly can be used to store a volume of a liquid buffer solution for use in a buffer management system.

In one embodiment, a biocontainer assembly includes a biocontainer bag, a shelf, and a capacitive fill level sensor. The biocontainer bag defines a storage volume. The shelf has a support surface configured to support the biocontainer bag. The support surface is disposed at an oblique angle with respect to a horizontal axis. The capacitive fill level sensor is mounted to the support surface. The capacitive fill level sensor is configured to generate a fill level signal indicative of the amount of material within the storage volume of the biocontainer bag.

In another embodiment, a biocontainer assembly includes a frame structure, an angled support member, and a capacitive fill level sensor. The frame structure includes a plurality of uprights. The angled support member includes a planar support surface configured to support a biocontainer bag defining an interior storage volume therein. The angled support member is mounted to the uprights of the frame structure such that the support surface is disposed at an incline angle with respect to a horizontal axis so that the biocontainer bag, when resting upon the support surface, is in an inclined storage position with respect to the horizontal axis. The capacitive fill level sensor is mounted to the angled support member such that the capacitive fill level sensor is positioned to detect a volume of material disposed within the biocontainer bag when the biocontainer bag is in the inclined storage position over a range of volumes between a minimum fill volume and a maximum fill volume.

In another aspect, the present disclosure is directed to embodiments of a method of using a biocontainer assembly. In one embodiment, a method of using a biocontainer assembly includes placing a biocontainer bag on a support surface of a shelf. The biocontainer bag defines a storage volume, and the support surface of the shelf is disposed at an oblique angle with respect to a horizontal axis. Using a capacitive fill level sensor, an amount of material within the storage volume of the biocontainer bag is detected. A fill level signal is transmitted from the capacitive fill level sensor to a controller. The fill level signal is indicative of the amount of material detected within the storage volume of the biocontainer bag.

Further and alternative aspects and features of the disclosed principles will be appreciated from the following detailed description and the accompanying drawings. As will be appreciated, the biocontainer assemblies and buffer management systems disclosed herein are capable of being carried out in other and different embodiments, and capable of being modified in various respects. Accordingly, it is to be understood that both the foregoing general description and the following detailed description are exemplary and explanatory only and do not restrict the scope of the appended claims.

Figure 1:
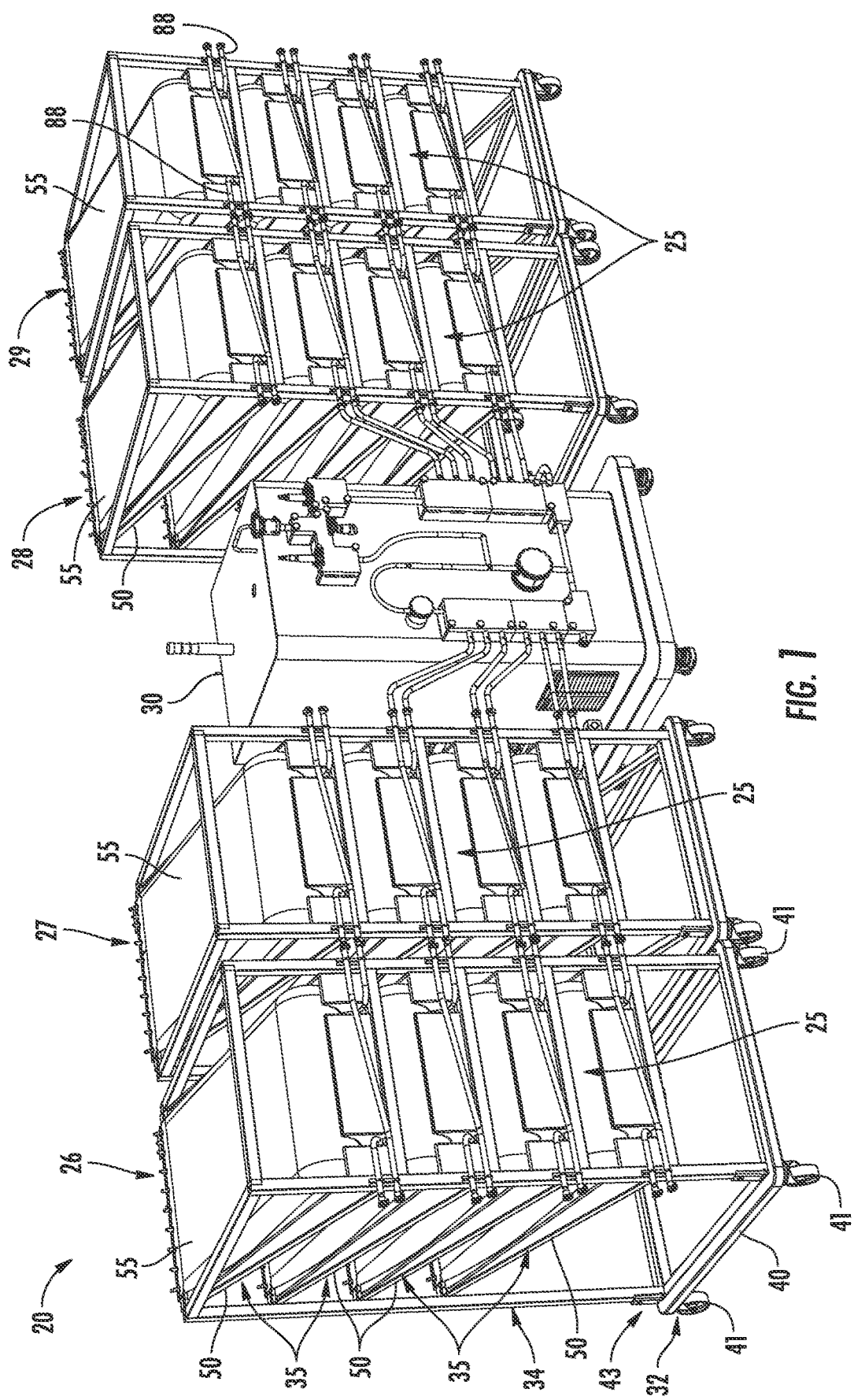
FIG. 1 is a perspective view of an embodiment of a buffer management system constructed in accordance with principles of the present disclosure that includes an embodiment of a biocontainer assembly constructed in accordance with principles of the present disclosure.

It should be understood that the drawings are not necessarily to scale and that the disclosed embodiments are illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF THE INVENTION

Embodiments of a biocontainer assembly constructed in accordance with principles of the present disclosure are adapted to be used with embodiments of a buffer management system constructed in accordance with principles of the present disclosure for a bioprocessing system. Embodiments of a biocontainer assembly constructed in accordance with principles of the present disclosure can be used with a buffer management system, which includes a plurality of biocontainer bags each storing a volume of a liquid buffer solution therein.

Embodiments of a biocontainer assembly constructed in accordance with principles of the present disclosure can be used in biopharmaceutical environments, but can be used in other industrial applications where different fluids, solutions, reagents and/or chemicals are stored for metering to process station. Embodiments of a biocontainer assembly constructed in accordance with principles of the present disclosure can be used to monitor the amount of material stored therein for use in a downstream processing application.

Embodiments of a biocontainer assembly constructed in accordance with principles of the present disclosure are configured as a relatively compact solution to achieve fill level measuring and monitoring in a given application. Embodiments of a biocontainer assembly constructed in accordance with principles of the present disclosure can include multiple biocontainer bags stacked in an efficient form (particularly relative to a conventional workstation configured to store a similar volume of liquid). Embodiments of a biocontainer assembly constructed in accordance with principles of the present disclosure can be used as a replacement for conventional systems using weigh scale equipment.

In embodiments of a biocontainer assembly constructed in accordance with principles of the present disclosure, the biocontainer assembly can include a biocontainer bag, an angled support member, and an electronic fill level sensor in the form of a capacitive fill level sensor. The biocontainer bag defines a storage volume. The angled support member includes a support surface configured to support the biocontainer bag in an inclined storage position with respect to a horizontal axis. The capacitive fill level sensor is mounted to the angled support member such that the capacitive fill level sensor is positioned to detect a volume of liquid disposed within the biocontainer bag when the biocontainer bag is in the inclined storage position over a range of liquid volumes between a minimum fill volume and a maximum fill volume. The capacitive fill level sensor configured to generate a fill level signal indicative of the amount of material within the storage volume of the biocontainer bag. In embodiments, the capacitive fill level sensor comprises a strip sensor configured to detect fill levels along the strip over a predetermined length.

Turning now to the FIGURES, there is shown in FIG. 1 an embodiment of a buffer management system 20 constructed in accordance with principles of the present disclosure that includes a plurality of biocontainer assemblies 25 constructed in accordance with principles of the present disclosure. In embodiments, the buffer management system 20 can include at least one embodiment of a biocontainer assembly 25 constructed according to principles of the present disclosure.

Figure 2:
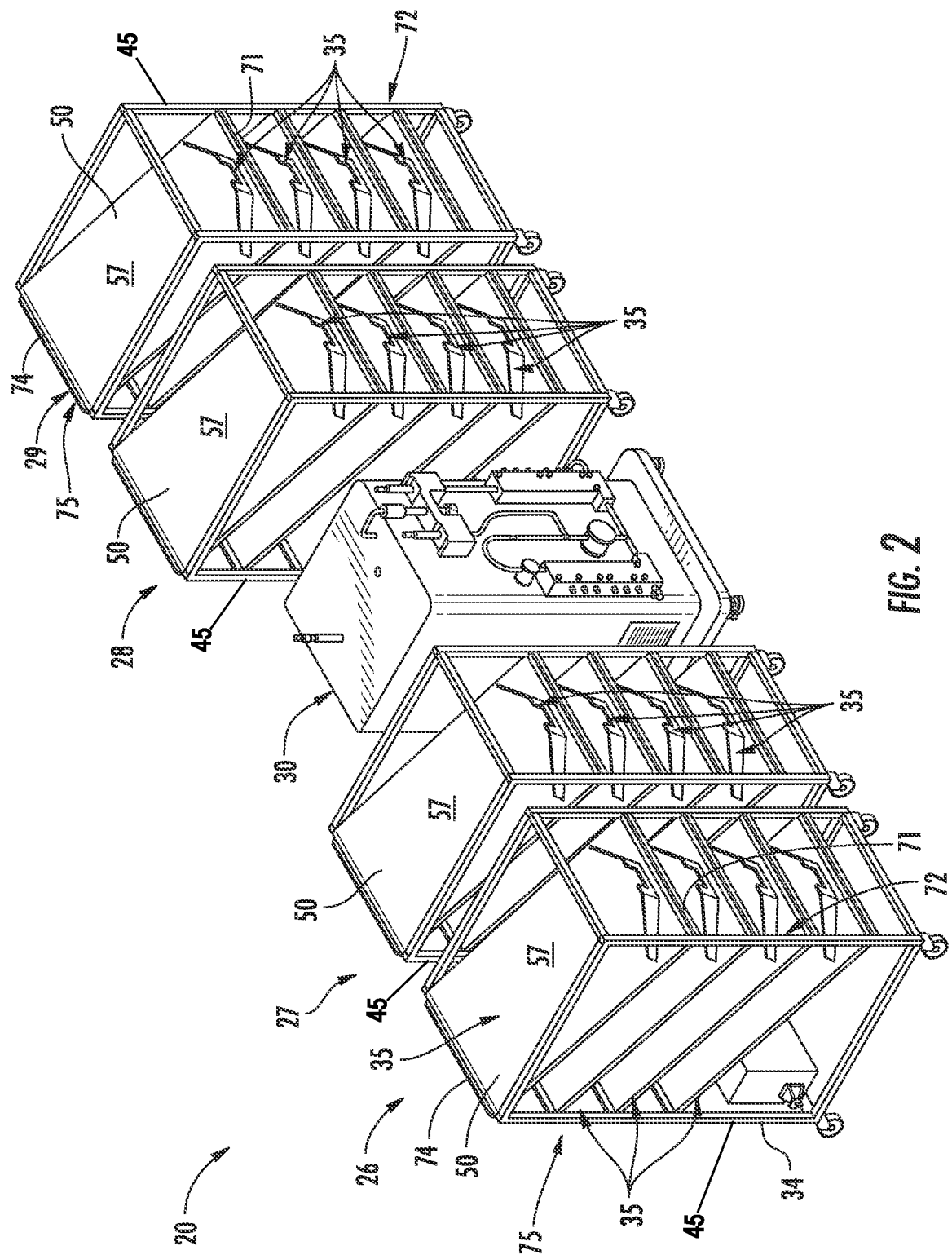
FIG. 2 is a top perspective view of the buffer management system of FIG. 1 with a plurality of biocontainer bags omitted for illustrative purposes.

Referring to FIGS. 1 and 2, in the illustrated embodiment, the buffer management system 20 includes a pair of biocontainer assemblies constructed according to principles of the present disclosure in the form of concentrated buffer rack towers 26, 27 configured to hold a supply of concentrated buffer solutions, an inline dilution skid 30 configured to produce a plurality of diluted buffer solutions for use in a bioprocessing application, and a pair of biocontainer assemblies constructed according to principles of the present disclosure in the form of diluted buffer rack towers 28, 29 configured to hold a supply of diluted buffer solutions. In other embodiments, the buffer management system 20 can include a different arrangement used to hold the supply of concentrated buffer solutions and/or the diluted buffer solutions. For example, in other embodiments, a buffer management system 20 constructed according to principles of the present disclosure can include at least one tower configured to hold one or more tanks filled with a concentrated buffer. In other embodiments, a buffer management system 20 constructed according to principles of the present disclosure can include at least one tower configured to hold one or more tanks filled with a diluted buffer.

Referring to FIG. 1, the rack towers 26, 27, 28, 29 of the buffer management system 20 are similarly constructed. Accordingly, it will be understood that the description of one rack tower 26, 27, 28, 29 is applicable to each of the other rack towers 26, 27, 28, 29, as well. Each of the illustrated biocontainer assemblies in the form of rack towers 26, 27, 28, 29 includes a trolley 32, a frame structure 34, and a plurality of bag fill level assemblies 35 constructed according to principles of the present disclosure. The frame structure 34 is connected to the trolley 32 and is configured to support a number of the bag fill level assemblies 35.

The trolley 32 includes a base 40 and a plurality of wheels 41 rotatably attached to the base 40. In the illustrated embodiment, the base 40 is rectangular, and there is a wheel 41 rotatably attached at each corner of the base 40. In embodiments, the base 40 can be substantially square-shaped. The base 40 of the trolley 32 is mounted to a bottom 43 of the frame structure 34.

Referring to FIG. 2, the frame structure 34 of each rack tower 26, 27, 28, 29 includes a plurality of uprights 45 connected to the trolley 32 and in spaced relationship to each other such that the uprights 45 can support a number of the bag fill level assemblies 35 in a vertical stacked relationship to each other. In the illustrated embodiment, each rack tower 26, 27, 28, 29 is configured to support four bag fill level assemblies 35 in a stacked relationship. In other embodiments, the rack tower 26, 27, 28, 29 can be configured to support a different number of bag fill level assemblies 35, including a single bag fill level assembly 35.

Referring to FIG. 1, each bag fill level assembly 35 is similarly constructed. Accordingly, it will be understood that the description of one bag fill level assembly 35 is applicable to each of the other bag fill level assemblies 35, as well. Each bag fill level assembly 35 includes a support member 50 in the form of an angled shelf mounted to the frame structure 34 of one of the various rack towers 26, 27, 28, 29 (see also, FIG. 2), an electronic fill level sensor 52 (see FIGS. 4 and 5) in the form of a capacitive fill level sensor, and a biocontainer bag 55 (see also, FIG. 3). In embodiments, each shelf 50 has associated therewith at least one electronic fill level sensor. In embodiments, each shelf 50 is configured to support a biocontainer bag 55 of a predetermined size.

Figure 4:
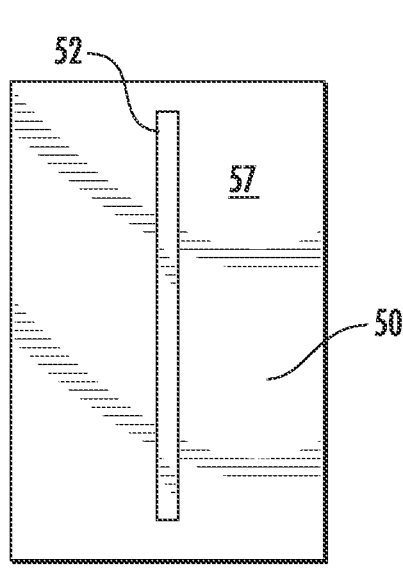
FIG. 4 is a top plan schematic view of an angled support member and a capacitive fill level sensor for use in embodiments of a biocontainer assembly constructed in accordance with principles of the present disclosure.
Figure 5:
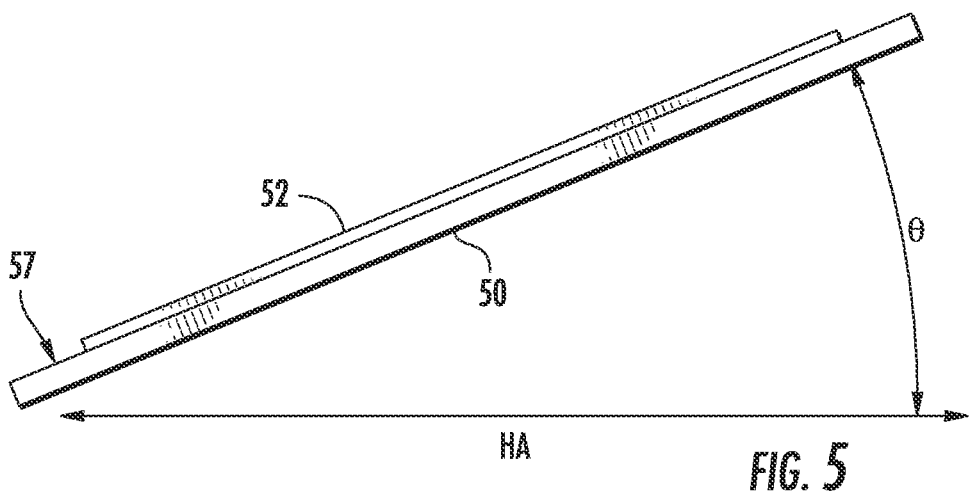
FIG. 5 is a side elevational view of the angled support member and the capacitive fill level sensor of FIG. 4.
Figure 7:
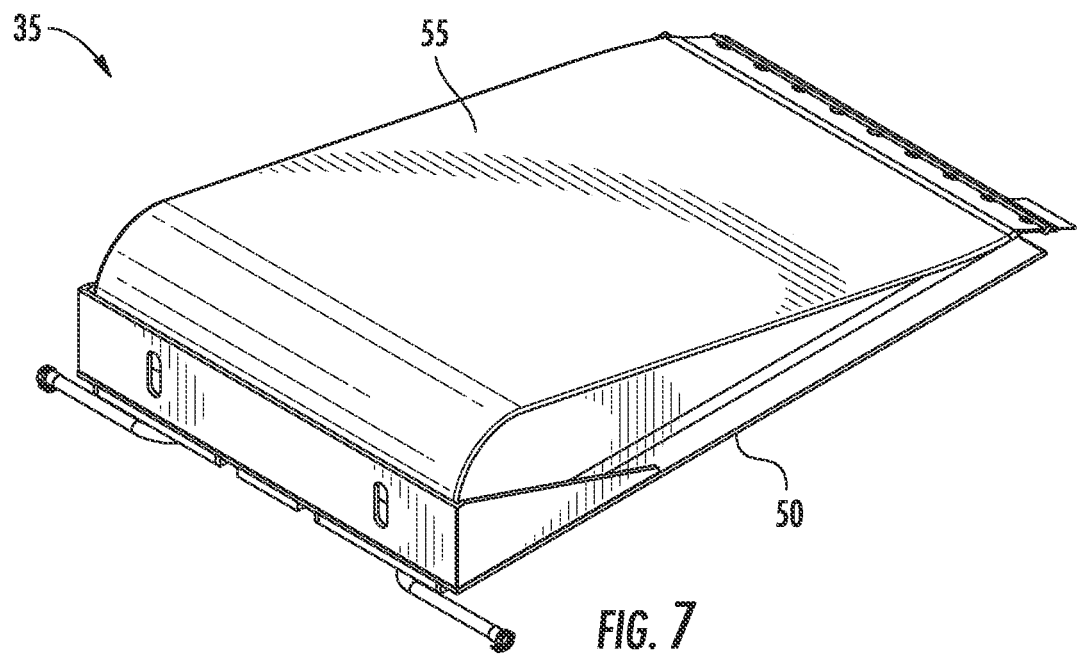
FIG. 7 is a top perspective view of an embodiment of a biocontainer bag fill level assembly constructed in accordance with principles of the present disclosure that is suitable for use in a buffer management system according to principles of the present disclosure.
Figure 8:
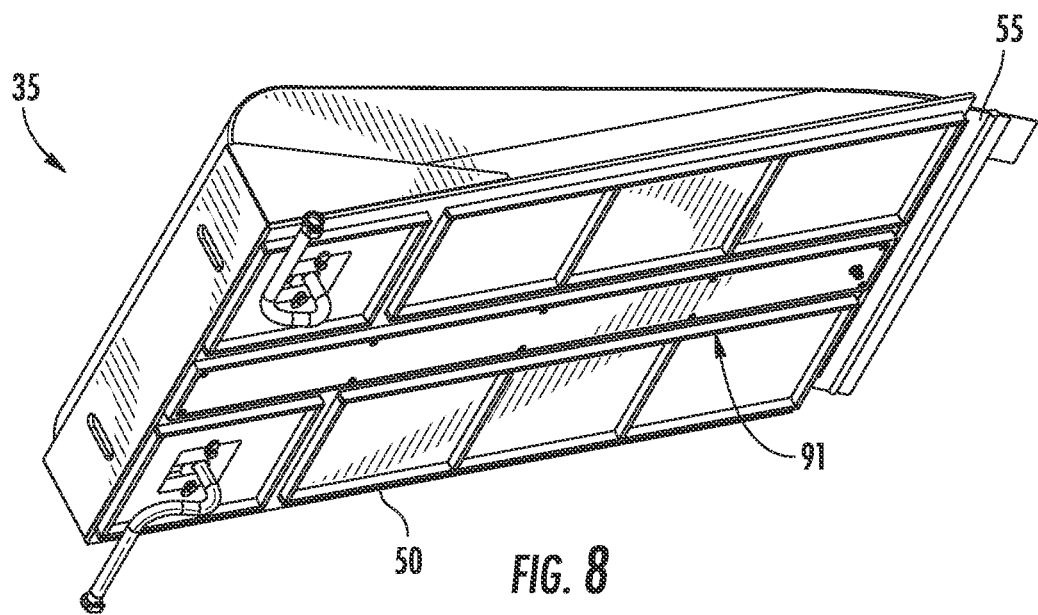
FIG. 8 is a bottom perspective view of the biocontainer bag fill level assembly of FIG. 7.

Referring to FIGS. 2, 4, and 5, in embodiments, the angled support member 50 includes a support surface 57 configured to support the biocontainer bag 55 in an inclined storage position with respect to a horizontal axis HA. In the illustrated embodiment, the frame structure 34 of each rack tower 26, 27, 28, 29 includes a series of angled shelves 50, each being pitched at an incline angle θ to a horizontal axis HA (see FIG. 5). The shelf 50 of each bag fill level assembly 35 is mounted to the uprights 45 such that the support surface 57 of each shelf 50 is disposed at the oblique angle with respect to a horizontal axis HA.

A lower end 71 of each shelf 50 is positioned at a front end 72 of the frame structure 34. An upper end 74 of each shelf 50 is positioned at a rear end 75 of the frame structure 34, which is in opposing relationship to the front end 72 of the frame structure 34. The lower end 71 of each shelf 50 is disposed vertically below the upper end 74 of the same shelf 50 when installed in the respective rack tower 26, 27, 28, 29.

Figure 3:
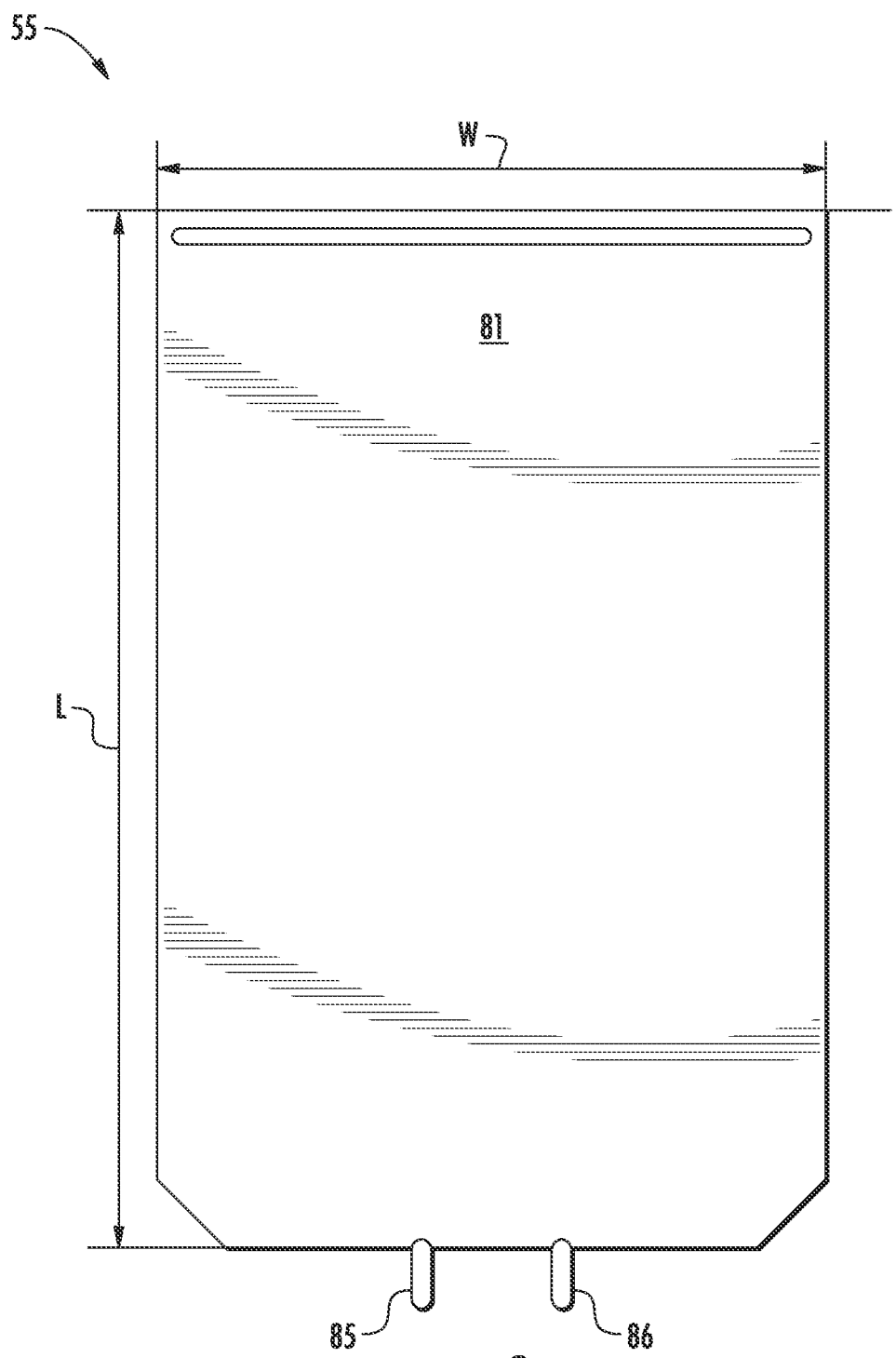
FIG. 3 is a plan view of an embodiment of a biocontainer bag suitable for use in embodiments of a biocontainer assembly constructed in accordance with principles of the present disclosure.

Referring to FIG. 3, in embodiments, the biocontainer bag 55 comprises any suitable container configured to store a predetermined volume of material for use in an intended application. In embodiments, the biocontainer bag 55 comprises a "2D" (or "two-dimensional") biocontainer bag, as is understood in the art, in which the width W and the length L of the biocontainer bag 55 determine how the fill level of liquid moves up the biocontainer bag 55 and is detected by the fill level sensor 52. In embodiments, the shape of the biocontainer bag 55 can be varied to adjust the rate at which the fill level changes in response to changes in the volume of the liquid stored therein. In embodiments, the biocontainer bag 55 comprises a suitable commercially-available single use biocontainer bag, such as, for example, those available from Pall Corporation of Port Washington, New York, under the brand name Allegro™ 2D biocontainer bags.

Figure 9:
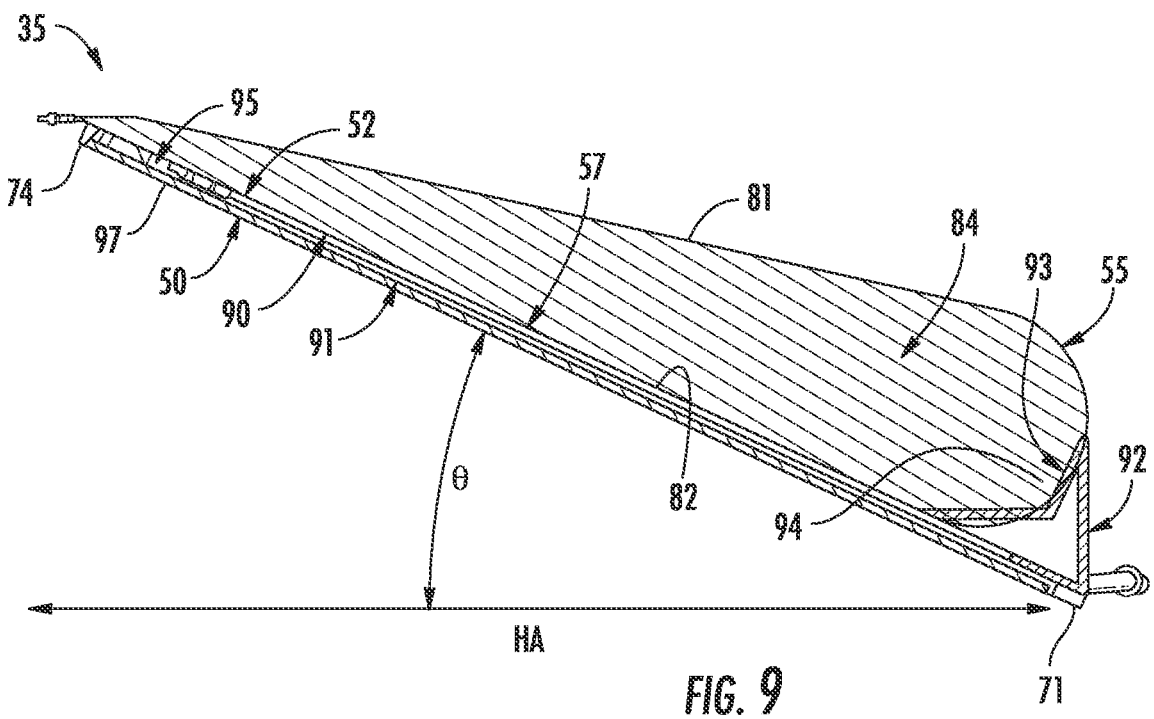
FIG. 9 is a longitudinal cross-sectional view of the biocontainer bag fill level assembly of FIG. 7.

Referring to FIGS. 3 and 9, in embodiments, the biocontainer bag 55 can include at least a pair of flexible panels 81, 82 that are connected together. The flexible panels 81, 82 cooperate together to define, at least in part, an interior storage volume 84 (see FIGS. 9 and 12) that is configured to hold a predetermined volume of material (e.g., one hundred liters). In embodiments, the biocontainer bag 55 can define therein a storage volume 84 of a predetermined size, such as one hundred liters, for example. In other embodiments, the storage volume 84 can be a different size.

In the illustrated embodiment, the biocontainer bag 55 comprises a 2D biocontainer bag made from a flexible film material. In embodiments, each panel 81, 82 is made from a suitable plastic material. For example, in embodiments, each panel 81, 82 is made of a low density polyethylene (LDPE) fluid contact and external film with an ethylene-vinyl alcohol copolymer (EvOH) gas barrier internal film. In embodiments, the biocontainer bag 55 can be made from a material that satisfies the requirements of at least one of: the USP <88> Biological Reactivity Tests, in vivo, for Class VI-50° C. Plastics that target-monitor the effect of the biocontainer's extracts for their systemic toxicity, tissue irritation, and biocompatibility for implantation; USP <87> Biological Reactivity Tests (in vitro) for plastics (cytotoxicity); and ISO 10993 Biological Evaluation of a Medical Device (Section 8.2.2: ISO 10993 Biological Evaluation of Medical Devices) in Section 4 (Hemolysis), Section 5 (Cytotoxicity), Section 6 (Implantation Test), Section 10 (Irritation and Sensitization Test), and Section 11 (Acute Systemic Toxicity).

Referring to FIG. 3, in embodiments, the biocontainer bag 55 defines at least one port 85 that is in fluid communication with the storage volume 84. In embodiments, the biocontainer bag 55 can include two or more ports 85, 86 and tubing 88 (see FIG. 1) with connector ends that are configured to receive material within the interior storage volume 84 of the bag 55 and/or discharge material from the bag 55. In embodiments, the biocontainer bag 55 includes at least one other port configured for use as a sampling port.

Referring to FIGS. 4 and 5, the support surface 57 of the angled support member 50 is configured to support the biocontainer bag 55 in an inclined storage position with respect to a horizontal axis HA (see, e.g., FIG. 1). The fill level sensor 52 is shown as being mounted directly to the support surface 57 of the support member 50. In embodiments of a biocontainer assembly according to principles of the present disclosure, the capacitive fill level sensor 52 is mounted to the support member 50 in any suitable manner which permits the fill level sensor 52 to detect the volume of material stored within the biocontainer bag 55 supported by the support member 50. The capacitive fill level sensor 52 can be mounted to the angled support member 50 such that the capacitive fill level sensor 52 is positioned to detect a volume of material disposed within the biocontainer bag 55 when the biocontainer bag 55 is in an inclined storage position over a range of volumes between a predetermined minimum fill volume and a predetermined maximum fill volume.

Referring to FIGS. 5 and 9, the support surface 57 of the support member 50 is generally planar and is disposed at an incline angle θ with respect to the horizontal axis HA. In the illustrated embodiment, the incline angle θ is twenty-five degrees. In embodiments, the incline angle θ of a support member 50 of a biocontainer assembly 25 constructed according to principles of the present disclosure can vary. In embodiments, the support surface 57 of the support member 50 of a biocontainer assembly 25 constructed according to principles of the present disclosure can be disposed at an incline angle θ with respect to the horizontal axis HA where the incline angle θ is in a range between five degrees and forty-five degrees, in a range between ten degrees and forty degrees in other embodiments, in a range between fifteen degrees and thirty-five degrees in yet other embodiments, and in a range between twenty degrees and thirty degrees in still other embodiments. In embodiments, the support surface 57 of the support member 50 of a biocontainer assembly 25 constructed according to principles of the present disclosure can be disposed at an incline angle θ with respect to the horizontal axis HA where the incline angle θ is in a range between twenty degrees and twenty-eight degrees, and in a range between twenty-two degrees and thirty degrees in still other embodiments. In embodiments, the support member 50 can be made from any suitable material, such as a suitable plastic or metal, for example.

One of ordinary skill in the art will appreciate that the incline angle θ can be varied according to the specific parameters of the application within which the biocontainer assembly 25 is intended to be used. For example, a shallow angle can be used in applications in which the range of material volume within the bag 55 that is desired to be monitored is less than the maximum fill volume of the biocontainer bag 55 being used in the biocontainer assembly. A steeper incline angle can be used in embodiments in which the resolution of the fill level sensor strip 52 is enhanced and/or it is desired to monitor smaller changes in volume.

In embodiments, the fill level sensor 52 is configured to generate a fill level signal indicative of the amount of material within the storage volume 84 of the biocontainer bag 55 as detected by the fill level sensor. In embodiments, the capacitive fill level sensor 52 can be used to measure the fill level of fluid media or of solids disposed within the storage volume 84 of the biocontainer bag 55. In embodiments, the capacitive fill level sensor 52 can be a suitable commercially-available strip sensor, such as those available from Balluff Ltd., which can detect fill levels along the strip over a predetermined length, such as, e.g. 850 mm. In the case of a capacitive fill level sensor 52 for measuring fill levels, the capacitive fill level sensor 52 can be configured to develop a measurement impedance in response to being within detection proximity of the material stored within the biocontainer bag 55, the ohmic component of which, including the capacitive component of which, reflects a measure for the fill level of the material within the storage volume 84 of the biocontainer bag 55 and which can be used to generate the fill level signal.

The combination and configuration of the components of the fill level assembly can be variable depending on the biocontainer volume and/or bioprocessing application requirements. For example, in embodiments, the support member 50 can be configured to support a plurality of biocontainer bags 55 with each such biocontainer bag 55 having associated therewith a respective electronic fill level sensor 52 mounted to the support member 50. In at least some of such embodiments, multiple narrower bags 55 can be mounted side by side on the support member 50, each with the same length L but different widths W' relating to different smaller volumes. Each of such biocontainer bags 55 can have associated therewith a respective fill level sensor 52 (such as, a fill level sensor strip or multiple sensor points, for example).

Figure 6:
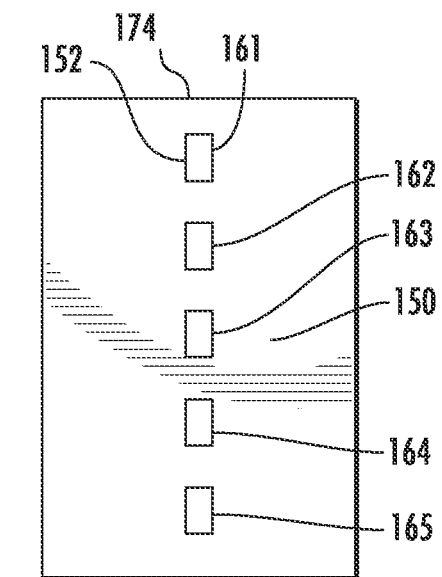
FIG. 6 is a top plan schematic view of an angled support member and a plurality of fill level sensors for use in embodiments of a biocontainer assembly constructed in accordance with principles of the present disclosure.

Referring to FIG. 6, in other embodiments, the biocontainer assembly can include a fill level sensor 152 that comprises multiple fill level sensors 161, 162, 163, 164, 165 arranged in a matrix and positioned at discrete positions corresponding to a desired control sequence, such as is shown in FIG. 6, for example. In embodiments, the multiple fill level sensors 161, 162, 163, 164, 165 can operate as on-off type sensors that provide a fill level signal indicative of a certain volume of liquid within the biocontainer bag 55 that can be used to manage the buffer solutions (e.g., a maximum fill position, a minimum fill position, and operational fill levels).

Referring to FIG. 6, the fill level sensor 152 comprises a plurality of fill level sensors 161, 162, 163, 164, 165 arranged in spaced relationship to each other. A first fill level sensor 161 is disposed at a first position corresponding to the predetermined maximum fill volume, and a second fill level sensor 165 is disposed at a second position corresponding to the predetermined minimum fill volume. In the illustrated embodiment, intermediate fill level sensors 162, 163, 164 are provided between the first fill level sensor 161 and the second fill level sensor 165 to provide addition sensing at intermediate fill volumes. The fill level sensors 161, 162, 163, 164, 165 are disposed in a linear arrangement running longitudinally along the shelf 150 from the rear end 174 to the front end 171 thereof. In other embodiments, the fill level sensors 161, 162, 163, 164, 165 can have a different arrangement with respect to each other. In other embodiments, the biocontainer assembly includes a different type of fill level sensor.

Figure 10:
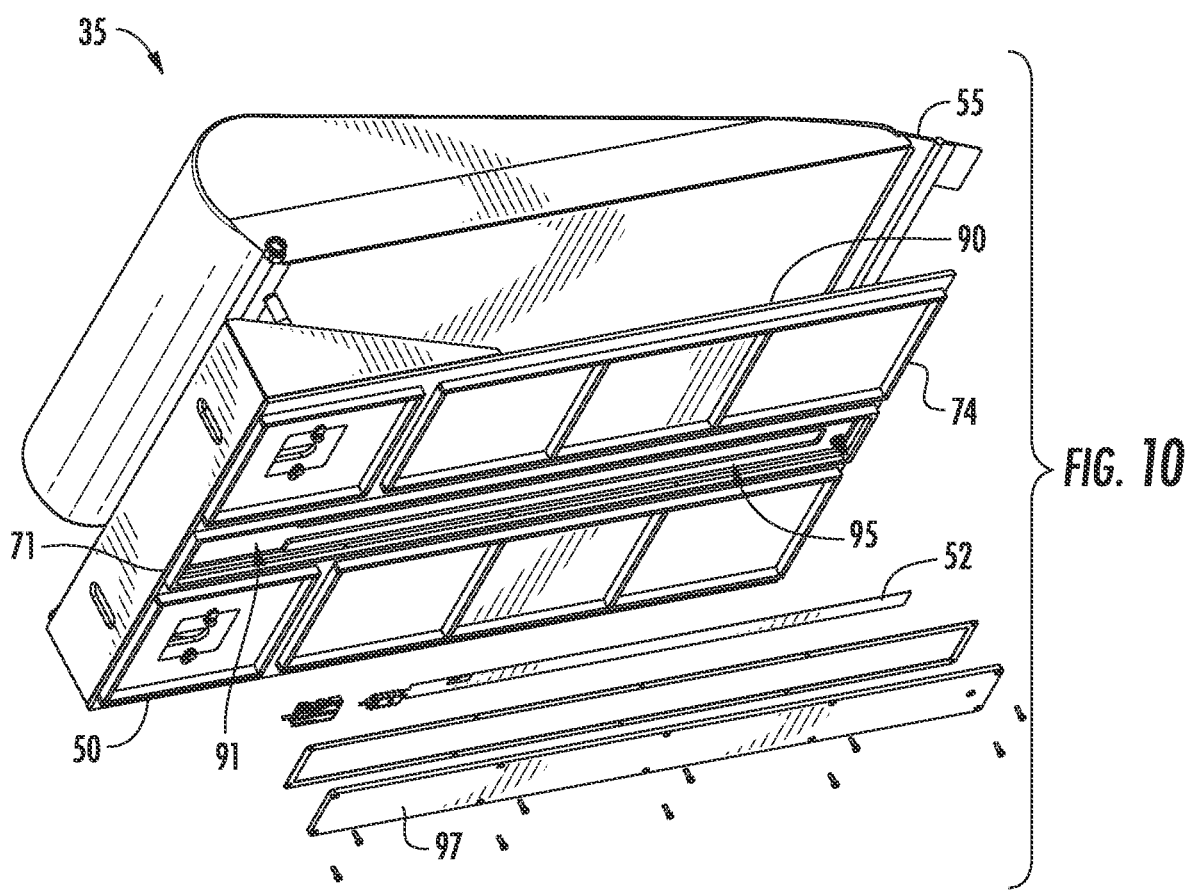
FIG. 10 is an exploded view, in perspective, of the biocontainer bag fill level assembly of FIG. 7.
Figure 11:
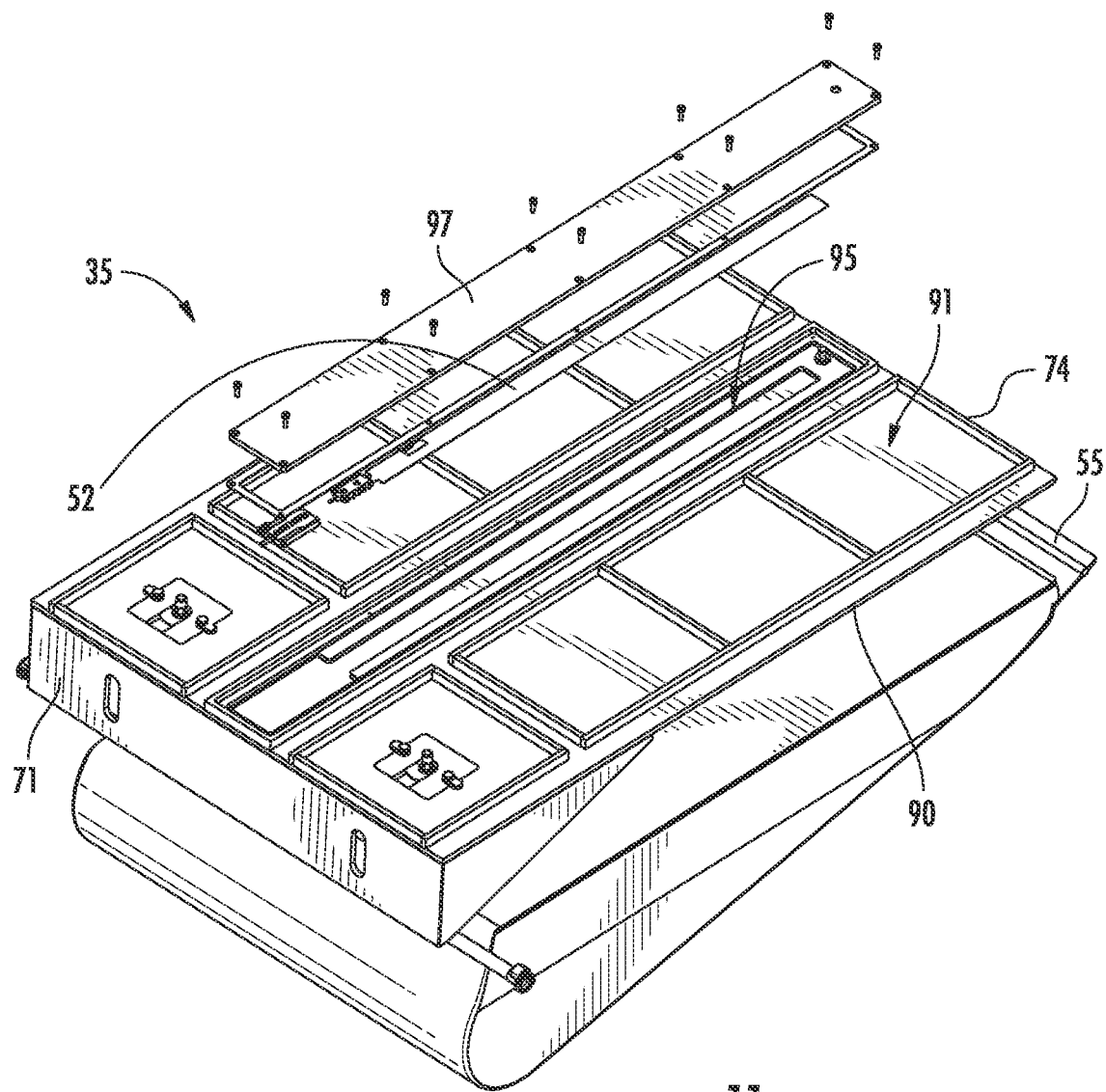
FIG. 11 is another exploded view, in perspective and from the bottom thereof, of the biocontainer bag fill level assembly of FIG. 7.

Referring to FIGS. 7-11, the bag fill level assembly 35 of the biocontainer assembly 25 includes the shelf 50 which is configured to support the 2D biocontainer bag 55 on an upper support panel 90 and to house the electronic fill level sensor 52 therein so that it is in close proximity to the underside 91 of the upper support panel 90 (see FIGS. 9-11).

Referring to FIG. 9, in the illustrated embodiment, the support member 50 includes a bag cradle 92 mounted to the front, lower end 71 of the shelf 50. The bag cradle 92 includes an angled support surface 93 configured to receive therein a bottom end 94 of the biocontainer bag 55 to help support the bag 55 and maintain it in position upon the shelf 50, particularly when the biocontainer bag 55 is filled with liquid as shown in FIG. 9.

Referring to FIG. 9, the capacitive fill level sensor 52 is configured to be mounted to the underside surface 91 of the shelf 50. The thickness of the shelf 50 from the underside 91 to the bag panel 82 resting upon the upper support panel 90 can be relatively thin, such as nominally 2 mm, such that the capacitive fill level sensor 52 can operate effectively to detect material stored within the biocontainer bag 55. In embodiments, the fill level sensor 52 has a maximum reading range along its length that can correspond to the bag geometry and the range of volume of material desired to be measured between a predetermined minimum fill level and a predetermined maximum fill level.

Referring to FIGS. 9-11, the capacitive fill level sensor 52 is mounted to the underside 91 of the upper support panel 90 with self-adhesive tape, positioned centrally from the upper shelf edge 74 to the lower shelf edge 71, such that the sensor 52 is in close proximity with the underside 91 of the upper support panel 90. In the illustrated embodiment, the underside 91 of the support panel 90 defines a recess 95 into which the capacitive fill level sensor can be disposed. A cover plate 97 can be provided which encloses the capacitive fill level sensor 52 within the recess 95, offering enhanced protection for the sensor 52 and presenting a neat appearance. The cover plate 97 is configured to be mounted to the underside 91 of the shelf 50 such that the cover plate 97 is over the recess 95.

In embodiments, the capacitive fill level sensor 52 includes an electrode unit having a strip-shaped measurement electrode, a strip-shaped counter electrode and a strip-shaped shielding electrode. In embodiments, the shielding electrode at least partially surrounds the measurement electrode. A first AC voltage source having a predefined frequency and amplitude is provided, to which the shielding electrode is connected such that a shielding capacitor formed between the shielding electrode and the measurement electrode has a shielding capacitance that is proportional to the length of the shielding electrode. A second AC voltage source of equal frequency and a predefined second amplitude is provided. The second amplitude is in phase opposition to the first amplitude, to which AC voltage source the counter electrode is connected, such that a measurement capacitor formed between the counter electrode and the measurement electrode has a measurement capacitance that is proportional to the fill level. The measurement electrode voltage present at the measurement electrode is used to determine the fill level. In embodiments, the capacitive fill level sensor 52 can be similar in other respect to the sensors disclosed in U.S. Patent Application Publication No. US2016/0047683, which is entitled, "Capacitive Fill Level Sensor," and which is incorporated herein in its entirety.

In embodiments, the capacitive fill level sensor 52 is configured to measure the fill level of a medium in the biocontainer bag 55. In the illustrated embodiment, the capacitive fill level sensor 52 is configured to detect liquid buffer solution disposed within the storage volume 84 as it fills up the container bag 55, filling from the bottom end 94 toward the top by virtue of the action of gravity upon the liquid.

Figure 12:
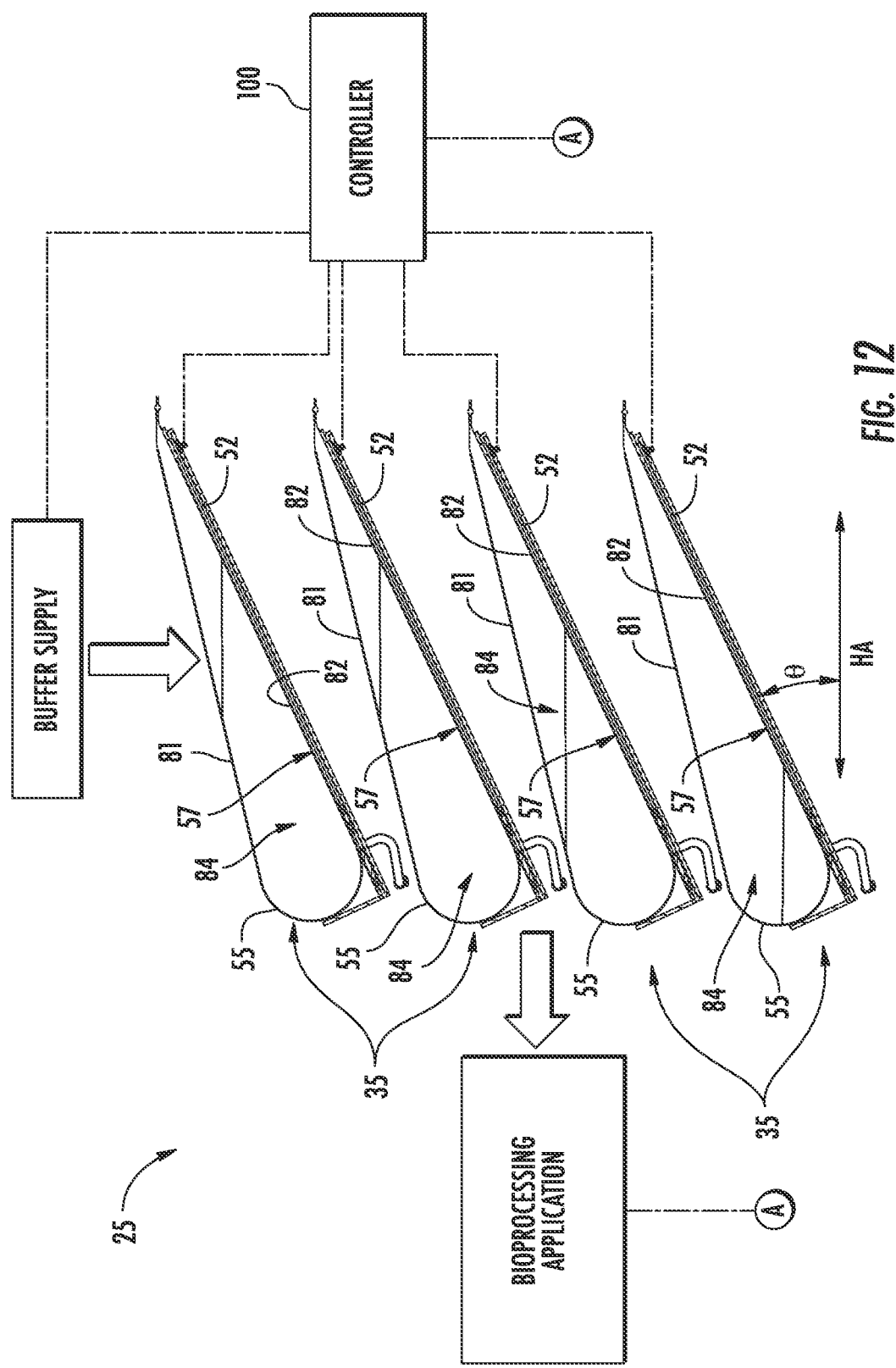
FIG. 12 is a series of longitudinal cross-sectional views of a biocontainer assembly including a plurality of a bag fill level assemblies constructed in accordance with principles of the present disclosure, illustrating a variety of fill positions of buffer solution in the respective biocontainer bags of the biocontainer assembly.

Referring to FIG. 12, the liquid level detected by the fill level sensor 52 of each fill level assembly 35 can be fed back via a fill level signal to a controller 100 (e.g., a suitable programmable logic controller (PLC)) of an automation system which creates a feedback loop. This loop can be used for a variety of buffer management functions as will be understood by one skilled in the art, such as, for example, to control pump liquid flow into the biocontainer bag for a range of functions.

Each bag fill level assembly 35 of the biocontainer assembly 25 can be used to measure automatically the level of material contained within the respective biocontainer bag 55. Each biocontainer bag 55 can be placed on a respective one of the shelves 55 in an inclined storage position (e.g., at an incline angle θ of 25 degrees to the horizontal axis HA) and be suspended by hooks at the upper edge of the bag 55. As liquid is introduced into each bag 55, the liquid displaces the flexible panels of the biocontainer bag 55 such that the bag 55 extends over the support surface 57 of the shelf 50, thereby promoting close proximity between the liquid disposed within the biocontainer bag 55 and the capacitive fill level sensor 52 associated with the particular shelf 50.

Referring to FIG. 12, the biocontainer assembly 25 can be configured to monitor the level of liquid within each biocontainer bag 55 of the assembly 25 as part of a bioprocessing application, such as a chromatography application or a tangential flow filtration (TFF) application, for example. The controller 100 is in operable arrangement with each of the capacitive fill level sensors 52 of the biocontainer assembly 25 to receive the respective fill level signal therefrom. The controller 100 is configured to control a volume management operation with respect to the amount of material within the storage volume 84 of the biocontainer bag 55 based upon the fill level signal received from the capacitive fill level sensor 52 respectively associated with each bag 55.

In embodiments, the buffer management system 20 is configured to use the fill level signal received from each capacitive liquid level sensor 52 of the biocontainer assemblies 25, 26, 27, 28 to monitor the volume of liquid stored within each bag 55 and to transmit this data to the controller 100 via a respective fill level signal, thus gaining real time feedback. The monitoring of the fill level signals can be used in the buffer management system 20 for various modes of operation. For example, in embodiments, the fill level signals from each bag fill level assembly 35 of the biocontainer assembly 26, 27, 28, 29 can be monitored during a filling sequence to ensure that each biocontainer bag 55 contains a desired volume of buffer solution therein before commencing a bioprocessing application. In embodiments, the controller 100 can be configured to determine the buffer solution levels in each biocontainer bag are within an acceptable range of volumes based upon the respective fill level signals and to fill a biocontainer bag 55 with additional buffer solution in the event that the fill level detected within the biocontainer bag 55 falls below a predetermined threshold. In embodiments, controller 100 can be configured to control, based upon the fill level signals received from the fill level assemblies 35, surge tanks in sequence to deliver a stable flow of buffer to a process unit of operation, such as a chromatography application or a tangential flow filtration (TFF) application, for example.

Embodiments of a biocontainer assembly constructed according to principles of the present disclosure can be used to carry out a method of managing a buffer solution as described above. In embodiments, a method using a biocontainer assembly following principles of the present disclosure can be used with any embodiment of a biocontainer assembly according to principles discussed herein.

In embodiments, a method of using a biocontainer assembly includes placing a biocontainer bag on a support surface of a shelf. The biocontainer bag defines a storage volume, and the support surface of the shelf is disposed at an oblique angle with respect to a horizontal axis. Using a capacitive fill level sensor, an amount of material within the storage volume of the biocontainer bag is detected. A fill level signal is transmitted from the capacitive fill level sensor to a controller. The fill level signal is indicative of the amount of material detected within the storage volume of the biocontainer bag. In embodiments, a volume management operation with respect to the amount of material within the storage volume of the biocontainer bag is performed using the controller based upon the fill level signal received from the capacitive fill level sensor All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A biocontainer assembly comprising:
   a biocontainer bag, the biocontainer bag defining a storage volume and having a bag width and bag length;
   a shelf, the shelf having a support surface configured to support the biocontainer bag, the support surface disposed at an oblique angle with respect to a horizontal axis and having a support width that is at least equal to the bag width and having a support length that is at least equal to the bag length;
   a capacitive fill level sensor, the capacitive fill level sensor mounted to the support surface, the capacitive fill level sensor configured to generate a fill level signal indicative of a volume of liquid within the storage volume of the biocontainer bag.

2. The biocontainer assembly according to claim 1, wherein the capacitive fill level sensor is mounted to the shelf such that the capacitive fill level sensor is positioned to detect the volume of liquid disposed within the storage volume of the biocontainer bag when the biocontainer bag is in an inclined storage position upon the support surface of the shelf over a range of volumes between a predetermined minimum fill volume and a predetermined maximum fill volume.

3. The biocontainer assembly according to claim 1, wherein the capacitive fill level sensor comprises a strip sensor configured to detect fill levels along the strip over a predetermined length.

4. The biocontainer assembly according to claim 1, wherein the capacitive fill level sensor comprises a plurality of fill level sensors arranged in spaced relationship to each other, a first fill level sensor being disposed at a first position corresponding to the predetermined maximum fill volume, and a second fill level sensor being disposed at a second position corresponding to the predetermined minimum fill volume.

5. The biocontainer assembly according to claim 1, wherein the oblique angle at which the support surface is disposed is in a range between five degrees and forty-five degrees.

6. The biocontainer assembly according to claim 5, wherein the oblique angle at which the support surface is disposed is in a range between fifteen degrees and thirty-five degrees.

7. The biocontainer assembly according to claim 1, wherein the shelf includes an upper end and a lower end, the lower end being disposed vertically below the upper end, and wherein the shelf includes a bag cradle mounted to the lower end, the bag cradle including an angled support surface configured to receive therein a bottom end of the biocontainer bag.

8. The biocontainer assembly according to claim 1, wherein the shelf includes an underside surface, and wherein the capacitive fill level sensor comprises a strip sensor configured to detect fill levels along the strip over a predetermined length, and wherein the capacitive fill level sensor is mounted to the underside surface.

9. The biocontainer assembly according to claim 8, wherein the underside surface of the shelf defines a recess, the capacitive fill level sensor disposed within the recess, and wherein the shelf includes a cover plate, the cover plate mounted to the underside of the shelf such that the cover plate is over the recess.

10. The biocontainer assembly according to claim 1, wherein the biocontainer bag includes a pair of flexible panels, the flexible panels being connected together, the flexible panels cooperate together to define, at least in part, the storage volume, the biocontainer bag defining a port, the port in fluid communication with the storage volume.

11. The biocontainer assembly according to claim 10 wherein the flexible panels of the biocontainer bag are made from plastic.

12. The biocontainer assembly according to claim 1, further comprising:
    a support frame, the support frame including a plurality of uprights, the shelf being mounted to the uprights such that the support surface of the shelf is disposed at the oblique angle with respect to a horizontal axis.

13. The biocontainer assembly according to claim 12, further comprising:
    a trolley, the trolley including a base and a plurality of wheels rotatably attached to the base, the base of the trolley mounted to a bottom of the frame structure.

14. The biocontainer assembly according to claim 12, wherein the biocontainer bag, the shelf, and the capacitive fill level sensor, comprise a first biocontainer bag, a first shelf, and a first capacitive fill level sensor, respectively, the biocontainer assembly the further comprising:
    a second biocontainer bag, the second biocontainer bag defining a storage volume;
    a second shelf, the second shelf having a support surface configured to support the biocontainer bag, the support surface mounted to the uprights of the support frame such that the support surface is disposed at an oblique angle with respect to a horizontal axis, the second shelf disposed in vertical spaced relationship to the first shelf;
    a second capacitive fill level sensor, the second capacitive fill level sensor mounted to the support surface of the second shelf, the second capacitive fill level sensor configured to generate a fill level signal indicative of the volume of liquid within the storage volume of the second biocontainer bag.

15. The biocontainer assembly according to claim 14, further comprising:
    a trolley, the trolley including a base and a plurality of wheels rotatably attached to the base, the base of the trolley mounted to a bottom of the frame structure.

16. A biocontainer assembly comprising:
    a frame structure, the frame structure including a plurality of uprights;
    an angled support member, the angled support member includes a planar support surface configured to support a biocontainer bag defining an interior storage volume therein and having a bag width and bag length, the planar support surface having a support width that is at least equal to the bag width and having a support length that is at least equal to the bag length, the angled support member being mounted to the uprights of the frame structure such that the planar support surface is disposed at an incline angle with respect to a horizontal axis so that the biocontainer bag, when resting upon the support surface, is in an inclined storage position with respect to the horizontal axis; and
    a capacitive fill level sensor, the capacitive fill level sensor mounted to the angled support member such that the capacitive fill level sensor is positioned to detect a volume of material disposed within the biocontainer bag when the biocontainer bag is in the inclined storage position over a range of volumes between a minimum fill volume and a maximum fill volume.

17. The biocontainer assembly according to claim 16, wherein the incline angle at which the support surface is disposed is in a range between five degrees and forty-five degrees.

18. A method of using a biocontainer assembly, the method comprising:
   placing a biocontainer bag on a support surface of a shelf, the biocontainer bag defining a storage volume and having a bag width and bag length, and the support surface of the shelf having a support width that is at least equal to the bag width and having a support length that is at least equal to the bag length and being disposed at an oblique angle with respect to a horizontal axis;
   detecting, using a capacitive fill level sensor, a volume of liquid within the storage volume of the biocontainer bag;
   transmitting a fill level signal from the capacitive fill level sensor to a controller, the fill level signal indicative of the volume of liquid detected within the storage volume of the biocontainer bag.

* * * * *